United States Patent
Smith

(10) Patent No.: US 9,901,510 B2
(45) Date of Patent: Feb. 27, 2018

(54) PORTABLE APPARATUS FOR PROVIDING CHEST THERAPY

(71) Applicant: Brett Gene Smith, Manhattan, KS (US)

(72) Inventor: Brett Gene Smith, Manhattan, KS (US)

(*) Notice: Subject to any disclaimer, the term of this patent is extended or adjusted under 35 U.S.C. 154(b) by 458 days.

(21) Appl. No.: 14/563,644

(22) Filed: Dec. 8, 2014

(65) Prior Publication Data

US 2015/0157532 A1    Jun. 11, 2015

Related U.S. Application Data

(60) Provisional application No. 61/913,409, filed on Dec. 9, 2013.

(51) Int. Cl.
*A61H 23/02* (2006.01)
*A61M 11/00* (2006.01)

(52) U.S. Cl.
CPC ... *A61H 23/0263* (2013.01); *A61H 2201/165* (2013.01); *A61H 2201/1619* (2013.01); *A61H 2201/501* (2013.01); *A61H 2201/5002* (2013.01); *A61M 11/00* (2013.01); *A61M 2205/05* (2013.01)

(58) Field of Classification Search
CPC .. A61H 23/00–23/04; A61H 2023/045; A61H 11/00–11/02; A61H 2201/1619–2201/1621; A61H 2201/165; A61H 2201/5002; A61H 2201/501; A61M 2205/05
See application file for complete search history.

(56) References Cited

U.S. PATENT DOCUMENTS

| | | | |
|---|---|---|---|
| 5,569,170 A | 10/1996 | Hansen | |
| 5,970,526 A * | 10/1999 | Weathers | A41F 9/002 2/311 |
| 6,155,996 A | 12/2000 | Van Brunt | |
| 6,234,985 B1 | 5/2001 | Lurie et al. | |
| 6,350,249 B1 | 2/2002 | Zicherman | |
| D456,591 S | 5/2002 | Hansen | |
| D461,897 S | 8/2002 | Hansen et al. | |
| 6,547,749 B2 | 4/2003 | Hansen | |
| 6,605,050 B2 | 8/2003 | Hansen | |

(Continued)

OTHER PUBLICATIONS

Mehta et al., Noninvasive Ventilation, American Journal of Respiratory and Critical Care Medicine, 163.2 (20010: 540-577.

(Continued)

*Primary Examiner* — Rachel Young
(74) *Attorney, Agent, or Firm* — Shook, Hardy & Bacon L.L.P.

(57) ABSTRACT

A portable apparatus for providing chest therapy to a user may include a wearable pack. A chest band may be coupled to the wearable pack. The chest band may include one or more chest band segments and may be configured to be worn around a chest of the user. A plurality of vibrating elements may be coupled to the one or more chest band segments. The plurality of vibrating elements may provide a vibrational force to the chest of the user when the chest band is worn around the chest of the user. The portable apparatus may further include a nebulizer treatment component, which may also be coupled to the wearable pack. A user input component may be electrically coupled to the plurality of vibrating elements and the nebulizer treatment component.

20 Claims, 14 Drawing Sheets

(56) References Cited

U.S. PATENT DOCUMENTS

| | | | |
|---|---|---|---|
| 6,676,613 B2 | 1/2004 | Cantrell et al. | |
| 6,676,614 B1 | 1/2004 | Hansen et al. | |
| 6,736,785 B1 | 5/2004 | Van Brunt | |
| 6,916,298 B2 | 7/2005 | VanBrunt et al. | |
| 6,958,047 B2 | 10/2005 | DeVlieger | |
| 7,018,348 B2 | 3/2006 | Van Brunt et al. | |
| 7,041,072 B2 | 5/2006 | Calvert | |
| 7,316,658 B2 | 1/2008 | Gagne | |
| 7,347,832 B2 | 3/2008 | Jensen et al. | |
| 7,374,550 B2 | 5/2008 | Hansen et al. | |
| 7,416,536 B2 | 8/2008 | DeVlieger | |
| 7,497,837 B2 | 3/2009 | Sherman et al. | |
| RE40,814 E | 6/2009 | Van Brunt et al. | |
| 7,618,384 B2 | 11/2009 | Nardi et al. | |
| 7,736,325 B2 | 6/2010 | Tung et al. | |
| 7,762,967 B2 | 7/2010 | Warwick et al. | |
| 7,785,280 B2 | 8/2010 | Kivisto | |
| 7,895,690 B2 | 3/2011 | Kovalyak | |
| D639,954 S | 6/2011 | Helgeson et al. | |
| 8,010,190 B2 | 8/2011 | Olson et al. | |
| 8,060,199 B2 | 11/2011 | Walker et al. | |
| 8,092,406 B2 * | 1/2012 | Gorsen | A61F 5/028 601/132 |
| 8,121,681 B2 | 2/2012 | Hampton et al. | |
| 8,192,381 B2 | 6/2012 | Nozzarella | |
| 8,202,237 B2 | 6/2012 | Helgeson et al. | |
| 8,226,583 B2 | 7/2012 | Ikeler et al. | |
| 8,298,165 B2 | 10/2012 | Sherman et al. | |
| RE44,187 E | 4/2013 | Marcovecchio et al. | |
| 8,408,204 B2 | 4/2013 | Lurie | |
| 8,460,223 B2 | 6/2013 | Huster et al. | |
| 8,540,653 B2 | 9/2013 | Baldauf et al. | |
| 8,663,138 B2 | 3/2014 | Huster et al. | |
| 8,708,937 B2 | 4/2014 | Van Brunt et al. | |
| 8,734,370 B1 | 5/2014 | Ignagni | |
| 8,740,824 B2 | 6/2014 | Hansen et al. | |
| 8,845,562 B2 | 9/2014 | Receveur et al. | |
| 8,845,564 B2 | 9/2014 | Cascini et al. | |
| 8,868,180 B2 | 10/2014 | Bystrom et al. | |
| 8,870,796 B2 | 10/2014 | Hoffmann | |
| 8,900,168 B2 | 12/2014 | Yamashiro et al. | |
| 9,549,869 B2 * | 1/2017 | DeVlieger | A61H 23/02 |
| 2004/0097850 A1 * | 5/2004 | Plante | A61H 23/0236 601/41 |
| 2005/0113725 A1 * | 5/2005 | Masuda | A61H 23/0263 601/72 |
| 2007/0246045 A1 * | 10/2007 | Hoffman | A61M 16/0057 128/204.18 |
| 2008/0021355 A1 * | 1/2008 | Huster | A61H 9/0078 601/149 |
| 2008/0027363 A1 * | 1/2008 | Brueckmann | A61H 23/0263 601/70 |
| 2012/0022415 A1 * | 1/2012 | Mullen | A61H 9/0078 601/150 |
| 2012/0035515 A1 | 2/2012 | Ng | |
| 2013/0226255 A1 | 8/2013 | Chapman et al. | |
| 2013/0261518 A1 | 10/2013 | Hansen et al. | |
| 2013/0267877 A1 | 10/2013 | Van Brunt | |
| 2013/0289456 A1 | 10/2013 | Chang Guo et al. | |
| 2013/0331747 A1 | 12/2013 | Helgeson et al. | |
| 2014/0012167 A1 | 1/2014 | DeVlieger et al. | |
| 2014/0024979 A1 | 1/2014 | Radbourne | |
| 2014/0171843 A1 | 6/2014 | Huster et al. | |
| 2014/0257151 A1 | 9/2014 | Chikkanaravangala et al. | |
| 2014/0257153 A1 | 9/2014 | Nickelson | |
| 2014/0276271 A1 | 9/2014 | Stryker et al. | |
| 2015/0025425 A1 | 1/2015 | Mitchell | |

OTHER PUBLICATIONS

Bach, John R., Mechanical Exsufflation, Noninvasive Ventilation, and New Strategies for Rehabilitation and Sleep Disordered Breathing, Bull. N.Y. Acad. Med., vol. 68, No. 2, Mar.-Apr. 1992, pp. 321-340.

Braverman, Jane M., Airway Clearance Needs in Duchenne Muscular Dystrophy: An Overview, Advanced Respiratory (2001), 8 pages.

Ciesla, Nancy D., Chest Physical Therapy for Patients in the Intensive Care Unit, Physical Therapy 76.6 (1996): 609-625.

AffloVest, Answering Needs: The Role of the AffloVest in the Respiratory Market, International Biophysics Corporation: AffloVest White Paper, 12 pages. Last Accessed Mar. 17, 2015 at: http://www.afflovest.com/wp-content/uploads/2013/06/White-Paper-on-AffloVest.pdf.

* cited by examiner

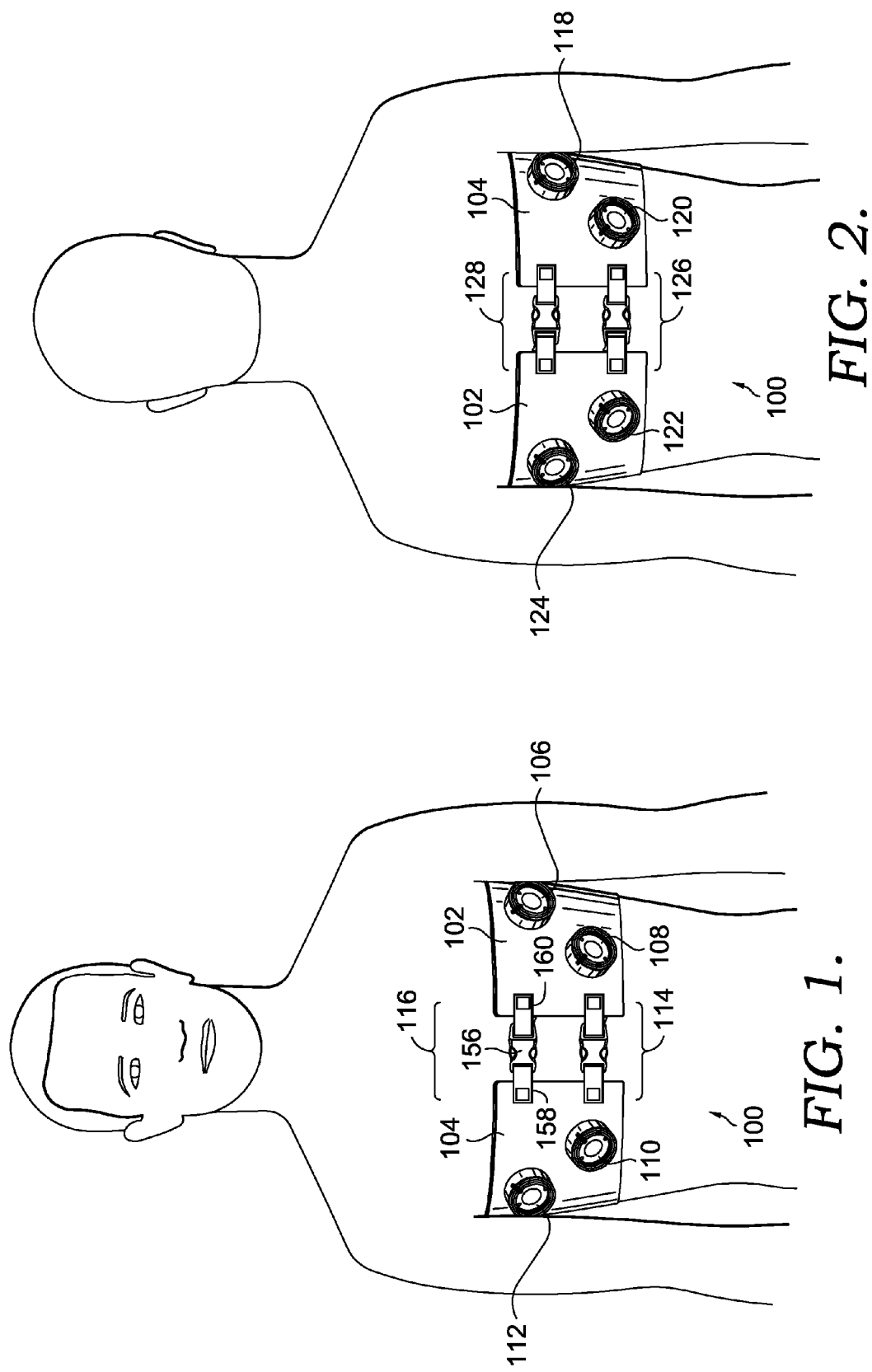

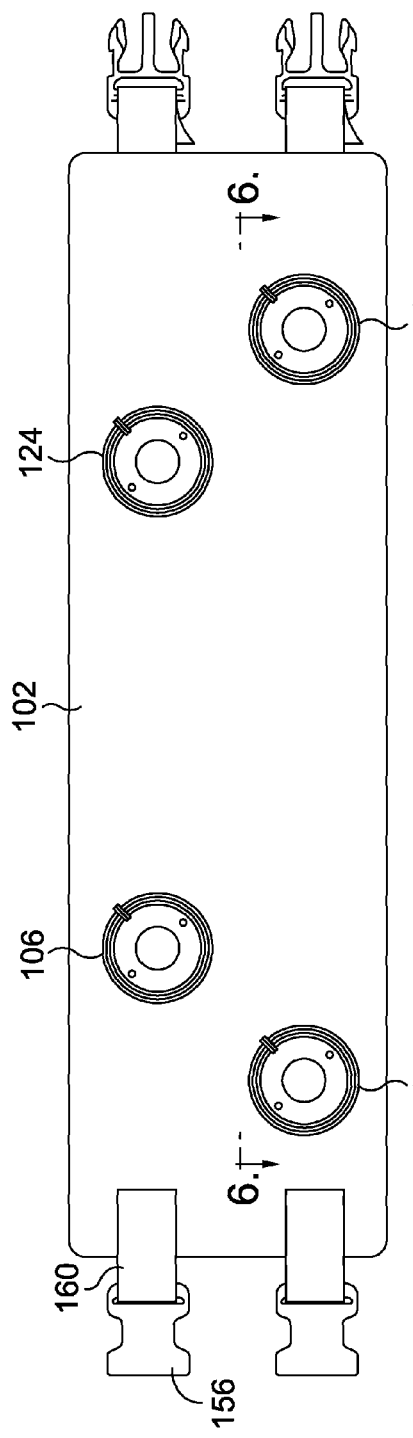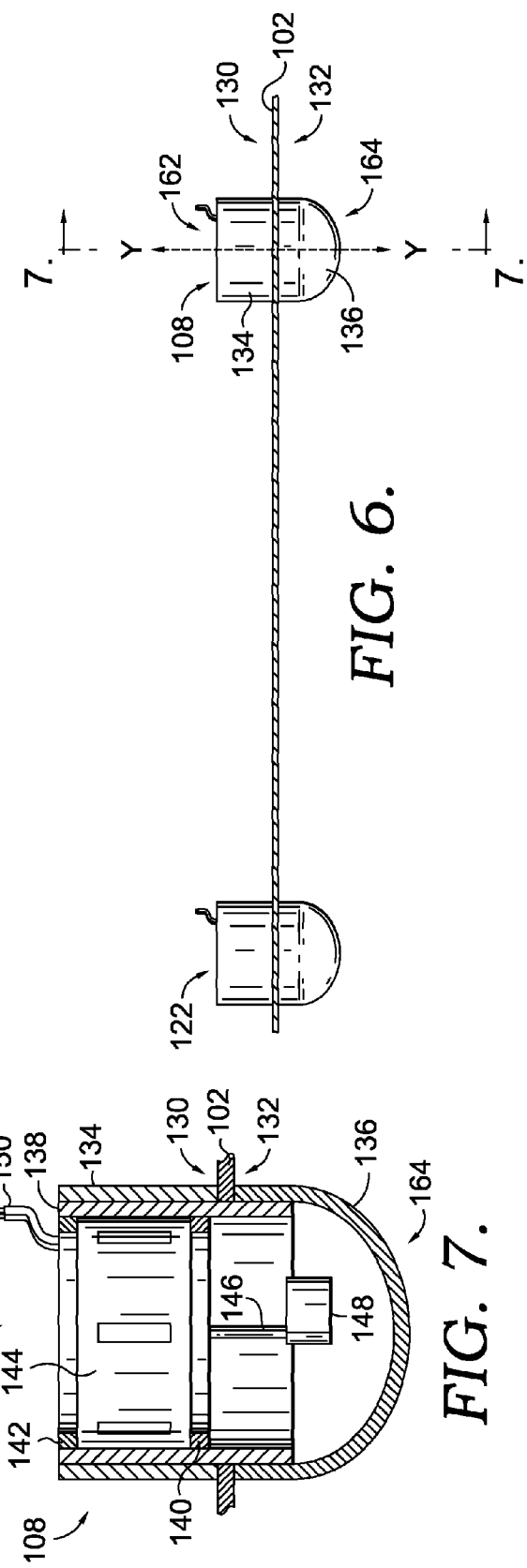
FIG. 5.
FIG. 6.
FIG. 7.

PORTABLE APPARATUS FOR PROVIDING CHEST THERAPY

CROSS-REFERENCE TO RELATED APPLICATIONS

This application claims priority to U.S. Provisional Application Ser. No. 61/913,409, filed Dec. 9, 2013 and entitled "Mobile Percussion Airway Clearance System," the disclosure of which is hereby incorporated by reference in its entirety.

BACKGROUND

Individuals having certain medical conditions may undergo chest physical therapy to aid with lung drainage and airway clearance. Such medical conditions include cystic fibrosis, bronchiectasis, neuromuscular diseases (e.g., Guillain-Barré syndrome), progressive muscle weakness (e.g., myasthenia gravis), and tetanus. Individuals having lung diseases, such as pneumonia, bronchitis, and certain forms of chronic obstructive pulmonary disease ("COPD"), including chronic bronchitis, may also benefit from chest physical therapy.

SUMMARY

This Summary is provided to introduce a selection of concepts in a simplified form that are further described below in the Detailed Description. This Summary is not intended to identify key features or essential features of the claimed subject matter, nor is it intended to be used as an aid in isolation to determine the scope of the claimed subject matter. Embodiments of the invention are defined by the claims below, not this Summary.

In brief and at a high level this disclosure describes, among other things, a portable apparatus for providing therapy, such as chest physical therapy to a user. In one example, the portable apparatus may include a chest band having one or more vibrating elements coupled thereto. When the chest band is worn by a user, the vibrating elements may be positioned adjacent to the user's chest and/or thorax in order to provide a vibrational force to various portions of the user's chest and/or thorax. This vibrational force may, among other things, improve lung drainage, mobilize lung secretions, and promote airway clearance.

DESCRIPTION OF THE DRAWINGS

The present disclosure makes reference to the attached drawing figures, wherein:

FIG. 1 is a front, perspective view of an exemplary chest band including vibrating elements, where the exemplary chest band is being worn by a user, in accordance with an exemplary embodiment hereof;

FIG. 2 is a rear, perspective view of an exemplary chest band including vibrating elements, where the exemplary chest band is being worn by a user, in accordance with an exemplary embodiment hereof;

FIG. 5 is a plan view of a top surface of an exemplary chest band segment, in accordance with an exemplary embodiment hereof;

FIG. 6 is a cross-section view of the exemplary chest band segment of FIG. 5, in accordance with an exemplary embodiment hereof;

FIG. 7 is an enlarged, cross-section view of an exemplary vibrating element of FIG. 6, in accordance with an exemplary embodiment hereof;

DETAILED DESCRIPTION

Figure 3:
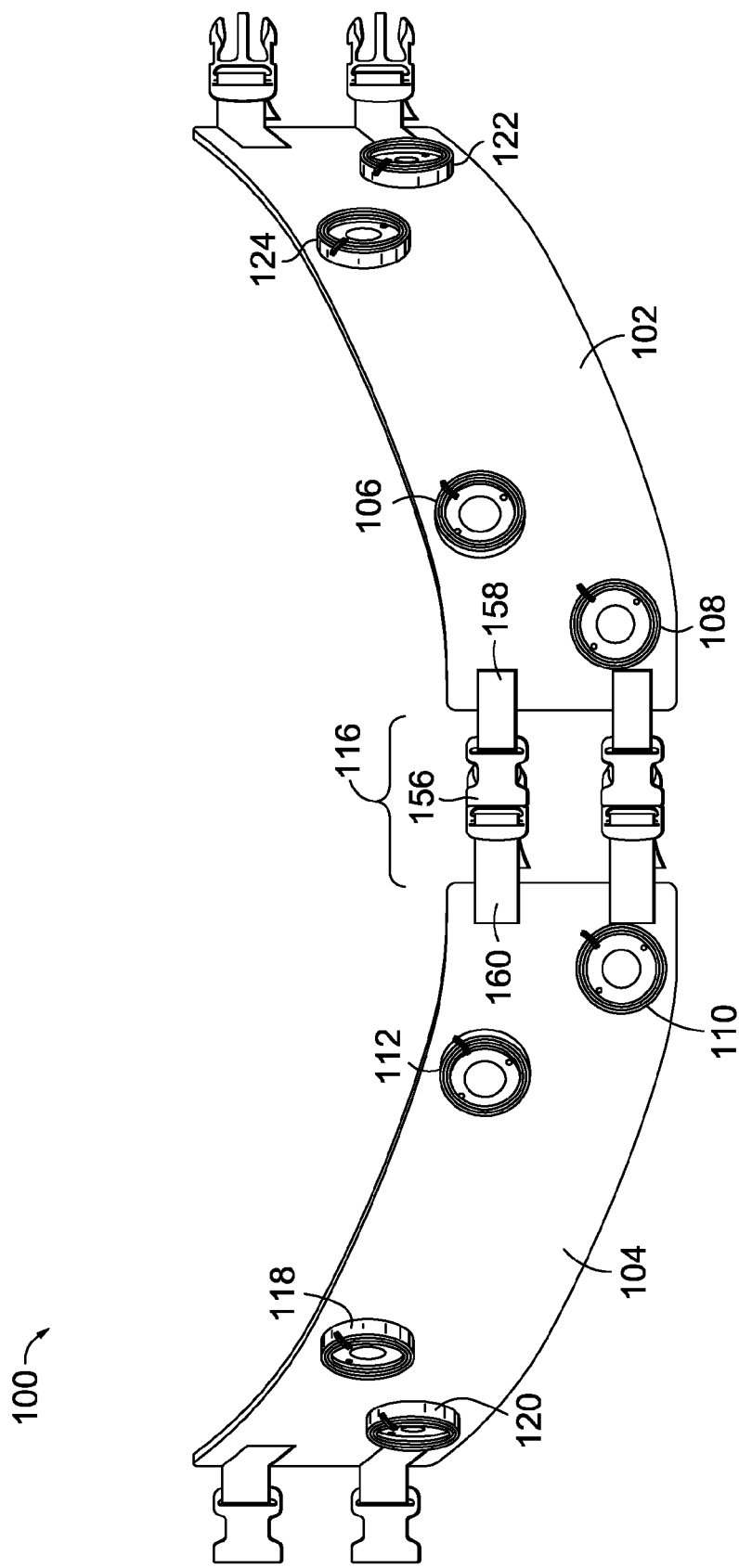
FIG. 3 is a front, perspective view of an exemplary chest band including vibrating elements, in accordance with an exemplary embodiment hereof.

The subject matter of select embodiments may be described with specificity to meet statutory requirements. But the description itself is not intended to necessarily limit the scope of the claims. Rather, the claimed subject matter might be embodied in other ways to include different components, steps, or combinations thereof similar to the ones described in this document, in conjunction with other present or future technologies. Terms should not be interpreted as implying any particular order among or between various steps disclosed herein unless and except when the order of individual steps is explicitly described.

For purposes of this disclosure, the word "including" has the same broad meaning as the word "comprising." In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

Embodiments of the invention include a portable apparatus for providing therapy, such as chest physical therapy, to a user. The therapy provided by the apparatus may improve lung drainage, mobilize lung secretions, and promote airway clearance. Exemplary embodiments of the invention may be described as a "Mobile Percussion Airway Clearance System" or "MPACS."

Individuals having certain medical conditions and/or diseases may benefit from the chest therapy provided by the features described herein. Such medical conditions include cystic fibrosis, bronchiectasis, neuromuscular diseases (e.g., Guillain-Barré syndrome), progressive muscle weakness (e.g., myasthenia gravis), and tetanus. Individuals having lung diseases, such as pneumonia, bronchitis, and certain forms of "COPD", including chronic bronchitis, may also benefit from chest physical therapy provided by the features described herein.

While the present disclosure focuses on chest physical therapy (which may be referred to herein as "chest therapy"), it will be understood by those having skill in the relevant art that the features described herein could be used for various other forms of physical therapy. Such other forms of physical therapy are included within the scope hereof.

An exemplary embodiment described herein may provide high-frequency chest wall percussions by way of a chest band including one or more vibrating elements. When the chest band is worn by a user, the vibrating elements may be positioned adjacent to the user's chest and/or thorax in order to provide a vibrational force to various portions of the user's chest and/or thorax. It is this force that may, among other things, improve lung drainage, mobilize lung secretions, and promote airway clearance.

A significant advantage of the portable apparatus including the features described herein is that it maximizes the mobility of the user while the user engages in a chest therapy session provided by the apparatus. To this end, the apparatus may be lightweight and portable. Accordingly, the user may engage in a chest therapy session provided by the apparatus while simultaneously participating in daily activities, such as cooking, walking, driving, cleaning, yard work, playing, and the like. The user may also engage in a chest therapy session provided by the apparatus while simultaneously participating in relatively strenuous activities, such as running, hiking, bike riding, exercising, and the like. Any encumbrance to the user during such daily and relatively strenuous activities is minimal. And because the apparatus is lightweight, portable, convenient, and comfortable, the user is likely to engage in chest therapy sessions more often than the user would if the user was required to use other devices that are heavier and more restrictive. Furthermore, the ability to exercise while engaging in a chest therapy session may provide particular advantages. For example, the chest therapy session might improve the user's ability to breath during exercise, thereby enhancing the user's exercise experience.

In one exemplary embodiment, the apparatus may include a wearable pack, where the wearable pack may be used to store and transport all components needed for chest therapy, as well as other types of therapy and/or treatment, such as nebulizer treatments. Even with these additional components, the apparatus may weigh approximately 8 pounds or less. Again, this enhanced mobility provides numerous benefits. For example, the user may easily carry the apparatus with him wherever he goes. The user need not return home (or to some other fixed location) in order to engage in a chest therapy and/or nebulizer treatment session. The user may maintain a physically and/or socially active schedule while also obtaining the benefits of frequent chest therapy sessions and nebulizer treatments. The apparatus may thereby provide psychological benefits due to significant lifestyle improvements.

A number of features provide the mobility advantages mentioned above. As already described, the apparatus may be lightweight and portable. Additionally, a portable power source, such as batteries, may be used to power the apparatus. As will be discussed in more detail below, a configuration of vibrating elements may maximize user mobility and minimize any physical interference caused by the apparatus. Additionally, a chest band may be comprised, at least in part, of elastic materials, thereby allowing a user to breathe normally during a chest therapy session. This exemplary feature, among others, allows a user to engage in strenuous activities that may result in heavy breathing while wearing the chest band.

Notably, exemplary embodiments hereof do not rely on pneumatic forces to provide chest therapy to a user. This may be advantageous, because the equipment required to provide such pneumatic force may be heavy, cumbersome, and power intensive.

This discussion of exemplary advantages is illustrative only and is not intended to be limiting. Based on the present disclosure, it will be understood that additional advantages are provided by a portable apparatus for providing therapy, as described herein.

Exemplary embodiments hereof include a portable apparatus for providing chest therapy to a user. The portable apparatus may include a wearable pack. A chest band including one or more chest band segments may be coupled to the wearable pack. The wearable pack may be configured to be worn around a chest of the user. A plurality of vibrating elements may be coupled to the one or more chest band segments. The plurality of vibrating elements may provide a vibrational force to the chest of the user when the chest band is worn around the chest of the user. The portable apparatus may further include a nebulizer treatment component coupled to the wearable pack. A user input component may be provided for receiving a user input regarding an operation of one or more of the nebulizer treatment component or the plurality of vibrating elements. The user input component may be electrically coupled to the plurality of vibrating elements and the nebulizer treatment component.

An additional embodiment includes a portable apparatus for providing chest therapy to a user. The portable apparatus may include a chest band segment including a top surface parallel to an opposite bottom surface. The bottom surface of the chest band segment may be configured to be positioned adjacent to a body of the user. A plurality of vibrating elements may be coupled to the chest band segment, where each of the plurality of vibrating elements provides a vibrational force.

Yet another embodiment provides an article of manufacture that includes a panel having a top surface that is parallel to an opposite bottom surface. The bottom surface may be configured to be positioned adjacent to a body of a user. A vibrating element may be coupled to the panel, where the vibrating element provides a vibrational force.

With reference now to the figures, components included in a portable apparatus for providing chest therapy to a user are described in accordance with embodiments of the invention. Various embodiments are described with respect to the figures in which like elements are depicted with like reference numerals.

Referring initially to FIG. 1, a front, perspective view of an exemplary chest band 100, where the exemplary chest band is being worn by a user, is provided. FIG. 2 provides a rear, perspective view of the exemplary chest band 100 being worn by the user. The chest band 100 may include one or more chest band segments, such as the chest band segments 102 and 104. Each chest band segment may include one or more vibrating elements. For example, the chest band segment 102 includes vibrating elements 106, 108, 122, and 124, and the chest band segment 104 includes vibrating elements 110, 112, 118, and 120. The vibrating elements may be uniform in size and/or shape. Additionally or alternatively, the vibrating elements may vary in size and/or shape. At the front of the user's body, the chest band segments 102 and 104 are coupled to one another by connection components 114 and 116. At the back of the user's body, the chest band segments 102 and 104 are coupled to one another by connection components 126 and 128.

As shown in FIGS. 1-2, one or more chest band segments may be coupled to one another to form a circumferential chest band. While the exemplary chest band 100 includes two chest band segments (chest band segments 102 and 104), any number of chest band segments is contemplated as being within the scope hereof. For example, a single chest band segment might wrap around the body of the user. In this case, one or more connection components may be needed in only one location in order to couple one end of the single chest band segment to the opposing end of the single chest band segment. In other examples, more than two chest band segments may be coupled to one another in order to form a chest band. In this instance, connection components may be used to couple one chest band segment to the next in order to form a continuous circumferential chest band. A chest band comprising multiple chest band segments may provide several advantages. For example, chest band segments having various uniform configurations may be manufactured, and each individual user may select a number of chest band segments having a desired configuration to serve the particular user's needs. For example, if a user has a relatively large chest circumference, the user might require several chest band segments, while a young child having a relatively small chest circumference might require fewer chest band segments. Additionally or alternatively, multiple sizes of chest band segments and/or chest bands might be provided. A further advantage of chest bands comprising multiple chest band segments is that a user may easily replace a single chest band segment that is malfunctioning. In other words, if one vibrating element on one chest band segment is not working, the user may simply replace that singular chest band segment with a new one, rather than incurring the expense of replacing the entire chest band.

The chest band segments 102 and 104 may be comprised of any type and/or number of materials. For example, a rigid and/or semi-rigid material, such as a plastic, may be used. Additionally or alternatively, a flexible material, such as a foam and/or elastic material, may be used. In some instances, any combination of rigid, semi-rigid, and flexile materials may be used to form a chest band segment.

The illustrative connection components 114, 116, 126, and 128 shown in the figures include a snap-fit buckle that joins two straps, each of which is coupled to a chest band segment. For example, connection component 116 includes a snap-fit buckle 156 that joins strap 158, which is coupled to the chest band segment 104, with strap 160, which is coupled to the chest band segment 102. The snap-fit buckle 156 may allow the length of strap 158 and/or strap 160 to be adjusted. The remaining connection components may provide similar features. In this way, the circumference of the chest band 100 may be easily adjusted and tailored to the size of a particular user. Additionally, the material comprising straps 158 and 160 may be elastic, such that the connection components may stretch in length. Advantageously, this allows the chest band 100 to fit snugly around the chest of the user, while also allowing the user to take deep breaths and cough. Thus, the user need not pause or discontinue treatment in order to breathe deeply or cough to expel mucus from the lungs. Accordingly, the user may engage in any number of activities while wearing the chest band and engaging in chest therapy.

Figure 18:
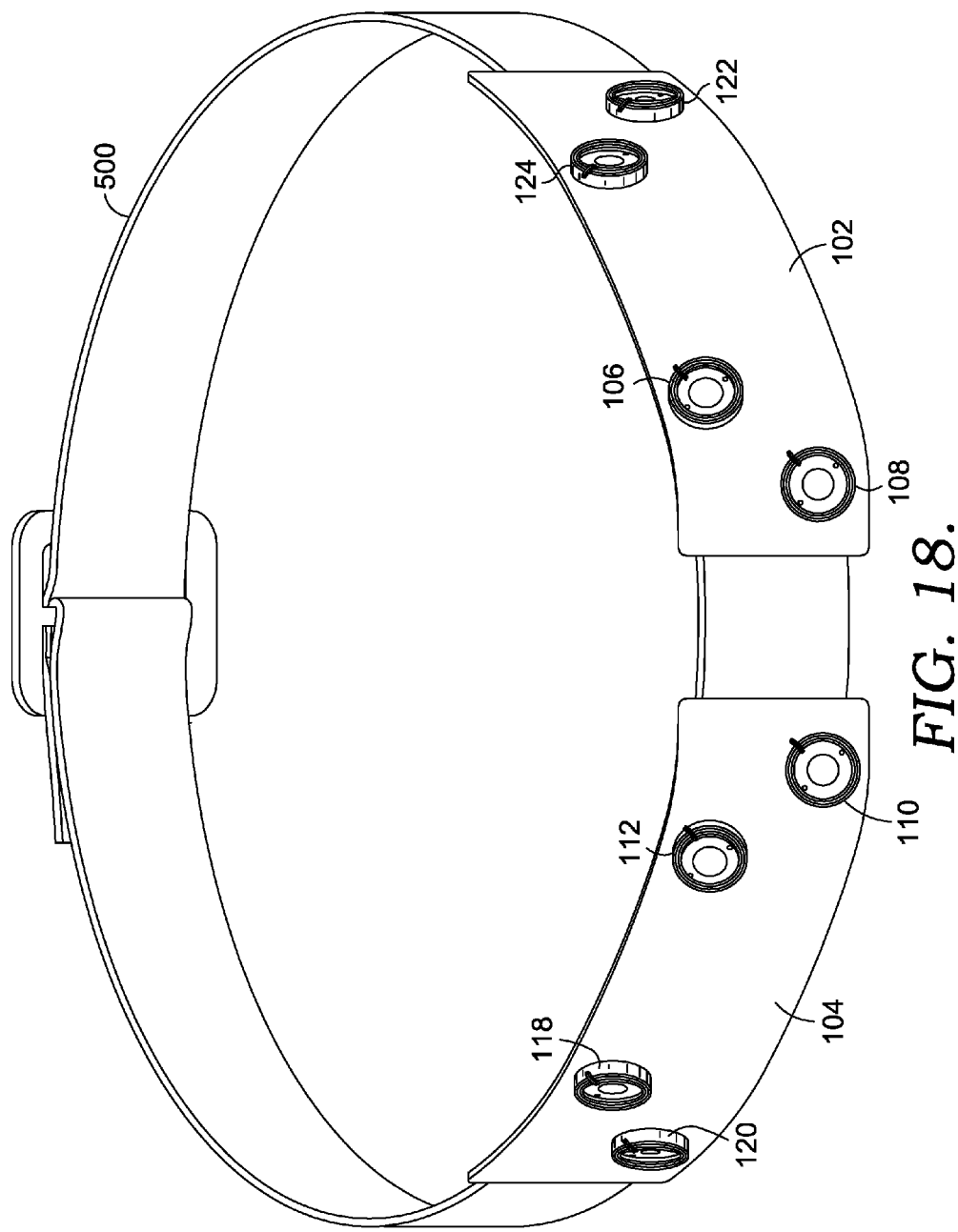
FIG. 18 is a front, perspective view of an exemplary belt on which chest band segments are mounted, in accordance with an exemplary embodiment hereof.

It will be understood that the connection components 114, 116, 126, and 128 are exemplary only, and that any number of other connection component configurations are included within the scope hereof. For example, the connection components may comprise clasps, belts, hook and loop fasteners, ties, laces, zippers, or any other means for connecting one chest band segment to another. Any combination of these components is included within the scope hereof. It will further be understood that the number of connection components illustrated in FIGS. 1-2 is exemplary only, and that any number of connection components may be used to connect one chest band segment to another. In some instances, the chest band segments may be mounted on a belt, such as an elastic belt, where the belt wraps around the chest of the user. Thus, in some instances, the chest band segments might not include connection components, but might instead be mounted on a belt or other item that may be secured around the user's chest. For example, FIG. 18 shows an exemplary belt 500 on which chest band segments 102 and 104 are mounted.

As shown in FIGS. 1-2, the vibrating elements 106, 108, 110, 112, 118, 120, 122, and 124 may be coupled to the chest band segments 102 and 104. When the user wears the chest band, the vibrating elements are positioned at various portions of the user's body, and when the vibrating elements are in operation, they provide a vibrational force to the user's body. The operation of the vibrating elements and the vibrational force provided to the user's body are discussed in more detail with respect to FIGS. 6-10 below, while exemplary configurations of the vibrating elements are discussed here with respect to FIGS. 1-2.

The vibrating elements may be positioned at particular locations on the chest band segments, such that when the chest band is worn by a user and the chest band segments are positioned adjacent to the user's body, the vibrating elements are located at a desired portion of the user's lung. For example, the vibrating elements may be placed according to particular lung lobe regions in order to provide a vibrational force to areas of the lung where mucus accumulates. The configuration of vibrating elements illustrated in FIGS. 1-2 is exemplary only. In other instances, the vibrating elements may be positioned at any location on the chest band segments 102 and 104.

The exemplary configuration shown in FIGS. 1-2 does, however, provide certain advantages, including enhanced mobility of the user while he is wearing the chest band. This enhanced mobility is at least partially attributable to the positioning of the upper vibrating elements, including vibrating elements 106, 112, 118, and 124, at a lateral area of the user's body, and the positioning of the lower vibrating elements, including vibrating elements 108, 110, 120 and 122, at a medial area of the user's body. As a user moves and swings his arm, the upper portion of his arm, near his armpit, has a more limited range of motion than a lower portion of his arm, near his elbow. Thus, as the user walks, runs, or engages in any number of activities, the lower portion of the user's arm may swing across the user's body or rub against the user's torso. The motion of the upper portion of the user's arm, by contrast, will be more limited. Accordingly, an upper vibrating element, such as the vibrating element 106, may be located at a lateral portion of the user's body and may have limited impact on the user's arm motions. Because the lower portion of the user's arm has a greater range of motion, a lower vibrating element, such as vibrating element 108, may be located at a medial portion of the user's body. Thus, as the user's arm moves next to the user's side, the user's arm is less likely to catch on and/or rub against the vibrating element 108, because it is located at a medial portion of the user's chest. Accordingly, the exemplary configuration depicted in FIGS. 1-2 allows the vibrating elements to be positioned at various portions of the user's lungs, while also maximizing the mobility of the user and allowing the user to swing his arms freely when the user is wearing the chest band.

Figure 4:
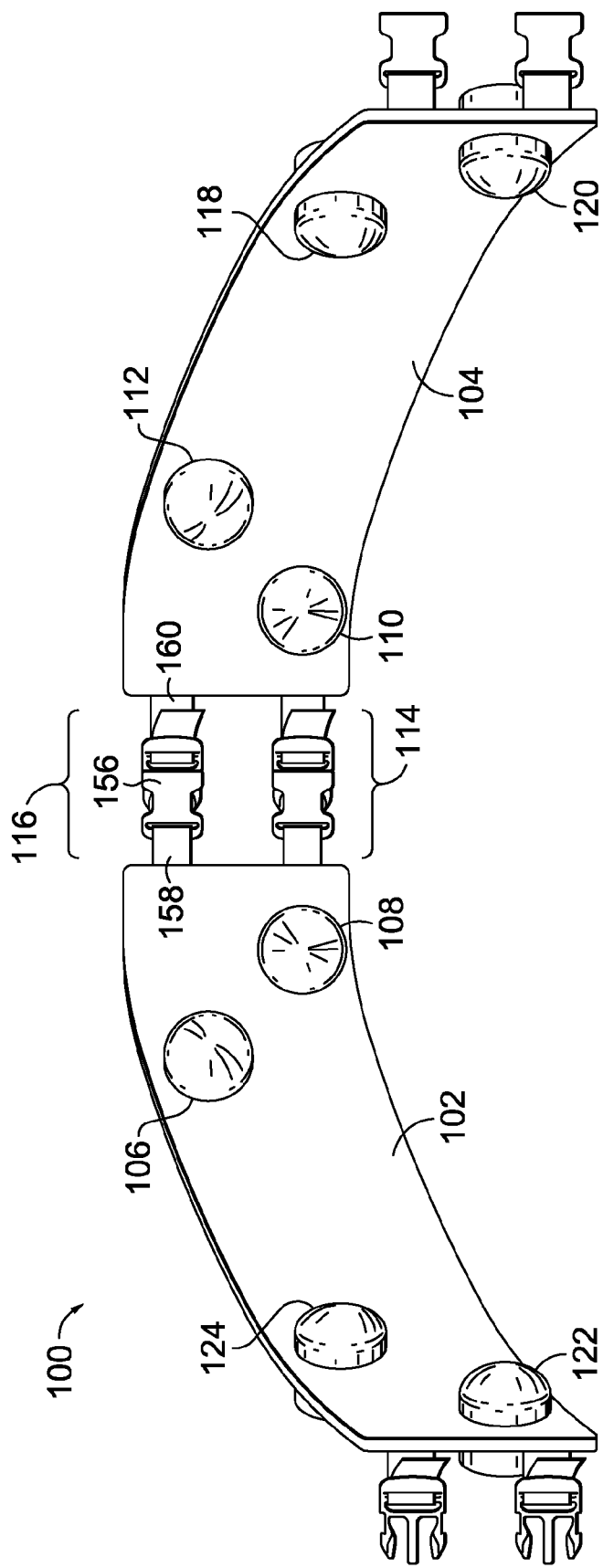
FIG. 4 is a rear, perspective view of an exemplary chest band including vibrating elements, in accordance with an exemplary embodiment hereof.

Turning now to FIGS. 3-4, a front, perspective view of the exemplary chest band 100 is provided in FIG. 3. The portion of the chest band 100 that is visible in FIG. 3 is the portion that may face away from the user when the user wears the chest band. In other words, it is the same portion that is visible in FIGS. 1-2. A rear, perspective view of the exemplary chest band 100 is provided in FIG. 4. The portion of the chest band 100 that is visible in FIG. 4 is the portion that may be adjacent to the user's body when the user wears the chest band 100. In other words, this portion of the chest band 100 is not visible when the user wears the chest band, because this is the portion that presses against the user's body.

FIG. 5 shows a plan view of a top surface of the exemplary chest band segment 102. FIG. 6 provides a cross-section view of the exemplary chest band segment 102 of FIG. 5. As shown in FIG. 6, the chest band segment may resemble a flat panel. In particular, the chest band segment 102 may include a top surface 130 that is parallel to an opposite bottom surface 132, such that the chest band segment forms a plane. The chest band segment 102 may be configured such that the bottom surface 132 is positioned adjacent to the user's body when the chest band segment 102 is in use. The vibrating elements 108 and 122 extend through the bottom surface 132 and the top surface 130 of the chest band segment 102. As can be seen in this cross-section view of FIG. 6, the vibrating elements 108 and 122 are maintained in a vertical position with respect to the planar surface provided by the chest band segment 102. This vertical positioning of vibrating elements will be discussed in greater detail below with respect to FIGS. 6-7, after the exemplary components that may be included in the vibrating elements are described with respect to the vibrating element 108 in FIGS. 8-10.

Figure 8:
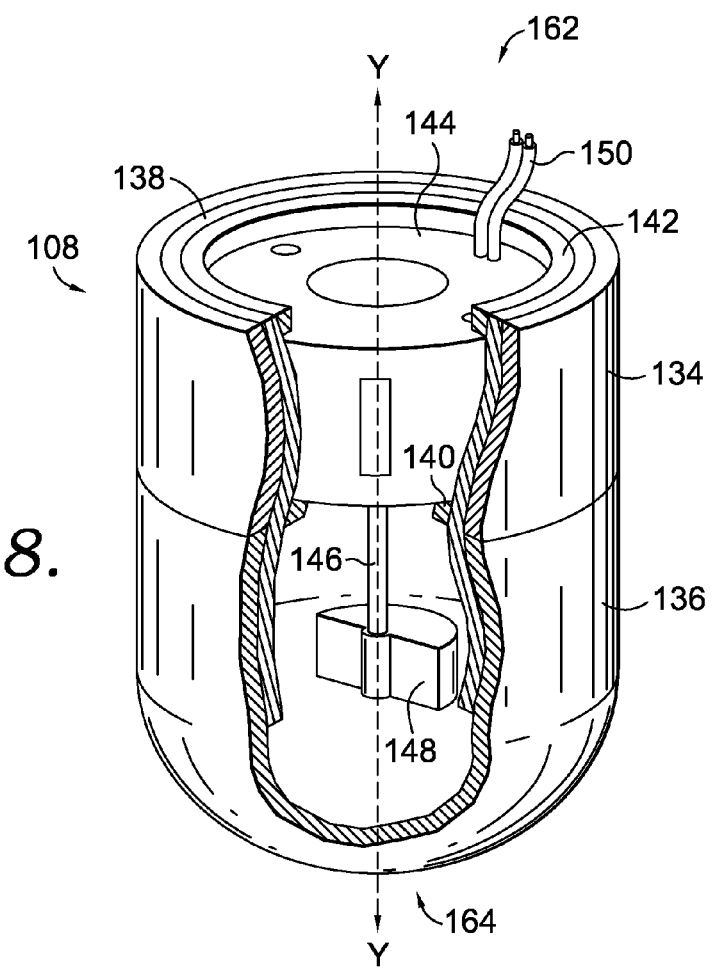
FIG. 8 is a cutaway view of an exemplary vibrating element, in accordance with an exemplary embodiment hereof.

A cutaway view of the exemplary vibrating element 108 is provided in FIG. 8. The vibrating element 108 may have a top end 162 and an opposite bottom end 164. In embodiments, the top end 162 and the bottom end 164 are axially opposed along a central vertical axis Y. The vibrating element may include a motor having various components, such as a motor body 144, a shaft 146, and a mass 148. A power connection 150 may provide power to the motor. The vibrating element 108 may further include a housing for the motor components. In particular, an inner housing 138 and an outer housing having an upper portion 134 and a lower portion 136 may be provided. The position of the motor body 144 may be maintained within the inner housing 138 by one or more positioning rings. For example, an upper positioning ring 142 may be positioned adjacent to the top of the motor body 144 at the top end 162 of the vibrating element 108. A lower positioning ring 140 may be positioned adjacent to the bottom of the motor body 144. In this way, the upper positioning ring 142 and the lower positioning ring 140 may maintain the motor body 144 at a desired position within the inner housing 138. The exemplary embodiment depicted in the figures includes an asymmetric outer housing. For example, the lower portion 136 of the outer housing, which is adjacent to the user's chest during use, may include a rounded surface that serves as a percussion cap. The percussion cap may enhance the user's comfort during chest physical therapy. For example, even if an intense vibrational force is provided to the user's body by the vibrating elements, the percussion cap may allow such force to be provided with minimal discomfort to the user. Other configurations of an outer housing are included within the scope hereof. In some instances, a symmetric outer housing may be used.

Figure 10:
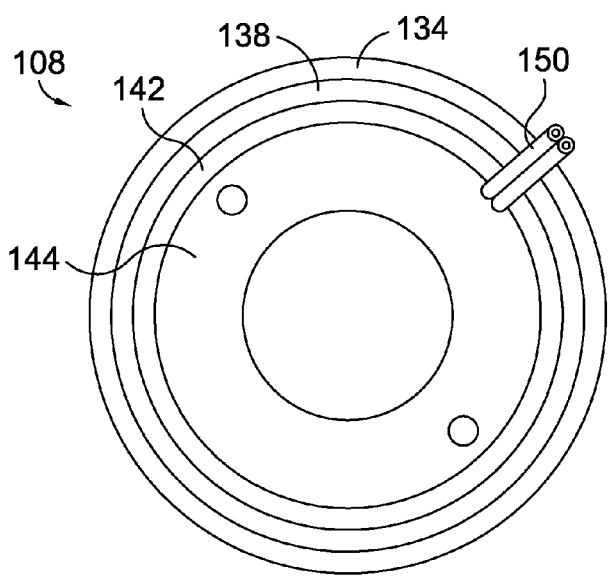
FIG. 10 is a top-down plan view of an exemplary vibrating element, in accordance with an exemplary embodiment hereof.
Figure 9:
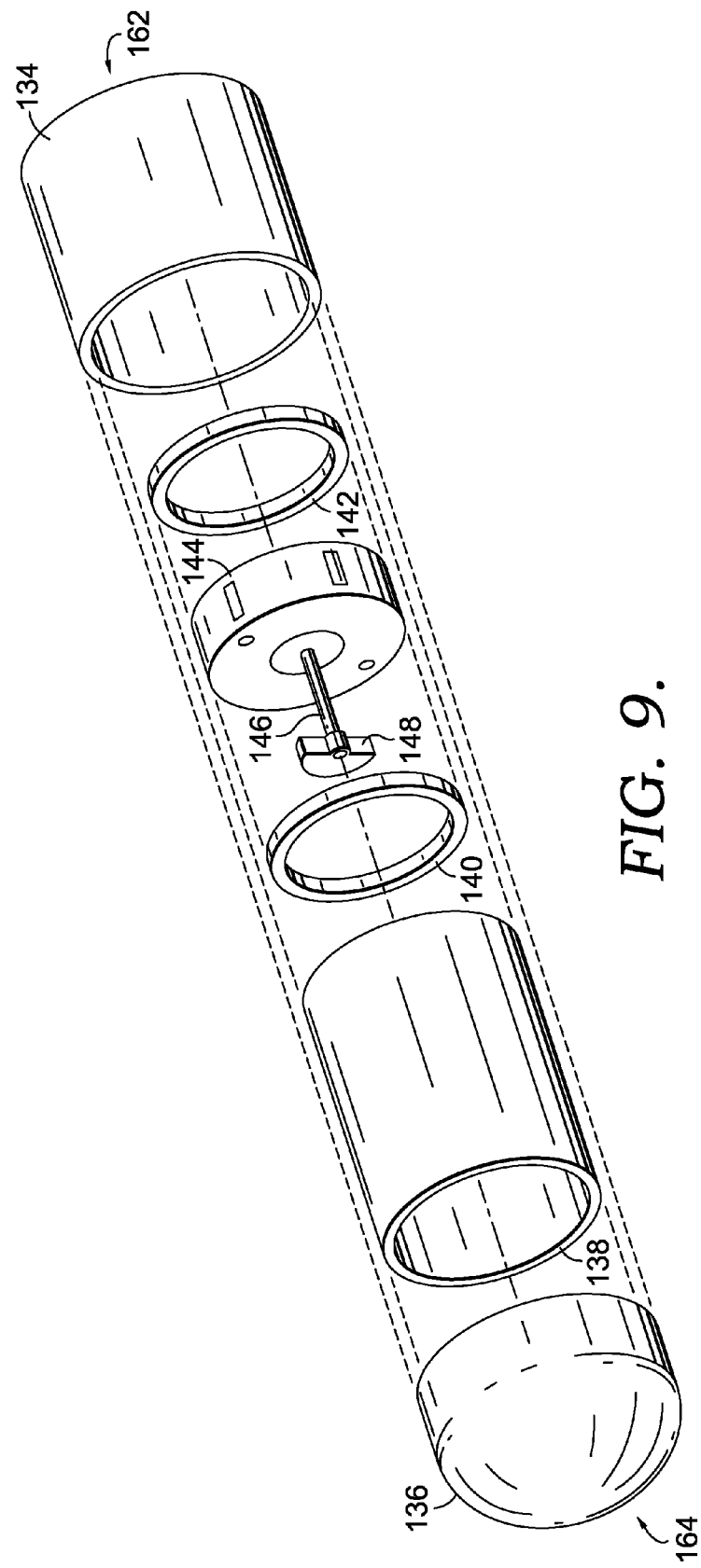
FIG. 9 is an exploded view of an exemplary vibrating element, in accordance with an exemplary embodiment hereof.

Each of the vibrating element components described with respect to FIG. 8 is also depicted in the exploded view of the vibrating element 108 provided by FIG. 9. As shown in FIG. 9, the upper positioning ring 142 and the lower positioning ring 140 may be positioned adjacent to a top surface and a bottom surface, respectively, of the motor body 144. The two positioning rings and the motor may fit within the inner housing 138. The outer housing upper portion 134 and the outer housing lower portion 136 may fit over the inner housing 138. FIG. 10 provides a top-down plan view of the exemplary vibrating element 108.

As mentioned, when the vibrating element 108 is in operation, it may provide a vibrational force. In particular, when power is supplied to the motor via the power connection 150, the mass 148 may be caused to rotate about the vertical axis Y. Due to the asymmetric configuration of the mass 148, as the mass 148 rotates, it causes displacement of the vibrating element 108. This displacement creates a vibrational force. The shaft 146 and the mass 148 may be allowed to rotate freely in order to maximize the vibrational force provided. The frequency at which the vibrating element 108 vibrates may be controlled by controlling the speed of the rotation of the mass 148. In one example, the vibrating element 108 may vibrate at a frequency between approximately 5 cycles per second and approximately 65 cycles per second (or between 5 hertz and 65 hertz). In another example, the vibrating element may vibrate at a frequency within a range of approximately 20 cycles per second to approximately 50 cycles per second (or 20 hertz to 50 hertz). In some embodiments, an "unbalanced motor," such as a low profile unbalanced motor, or a "vibration motor" may be included in the vibrating element. For example, the "Uni Vibe™ 24 mm Vibration Motor—13 mm Type," having a rated operating voltage of 12V and offered for sale by Precision Microdrives™, may be included in the vibrating element 108.

Returning now to FIG. 6, the vertical positioning of the vibrating elements 108 and 122 with respect to the planar surface provided by the chest band segment 102 will be discussed. As illustrated in FIG. 6, the vibrating element 108 may extend through the bottom surface 132 and the top surface 130 of the chest band segment 102. In particular, the vibrating element may extend vertically through these surfaces, such that the vibrating element 108 is maintained in a vertical position with respect to the planar surface provided by the chest band segment 102. In one instance, a vertical position may be characterized by the central vertical axis Y being approximately perpendicular to the planar surface provided by the chest band segment. As used herein, the terms "approximately" or "substantially," when used to describe a quantity and/or value, include a range of 85% to 115% of the specified quantity and/or value. For example, according to the statement above, if an angle between the vertical axis Y of the vibrating element 108 and the planar surface provided by the chest band segment 102 ranges between 76.5° and 103.5° (i.e. 85% and 115% of 90°, respectively), the central vertical axis Y of the vibrating element 108 may be described as "approximately" or "substantially" perpendicular to the planar surface provided by the chest band segment 102.

This vertical positioning may provide numerous advantages. One such advantage is that when the bottom end 164 of the vibrating element is positioned adjacent to the user's body, the vibrating element provides a vibrational force to the user's body. In particular, as the mass 148 rotates, the vibrating element 108 shakes and creates a percussive and/or tapping force on the user's body. This vibrational force may aid in loosening mucus in the user's lungs and clearing the user's airways. If the vibrating element was positioned horizontally, such that the vertical axis Y of the vibrating element 108 was parallel to the planar surface provided by the chest band segment 102, the vibrating element 108 might provide a "stroking" force, but it would not provide the vibrational force that is provided by the vertical orientation shown in FIG. 6. Nonetheless, in some instances, one or more vibrating elements may be positioned approximately parallel to the planar surface provided by the chest band segment 102.

In an exemplary embodiment, the vibrating element 108 is maintained in a vertical position with respect to the chest band segment 102 by, at least in part, a coupling between the housing for the vibrating element 108 and the chest band segment 102. As shown, the upper portion 134 of the outer housing is positioned adjacent to the top surface 130 of the chest band segment 102 and the lower portion 136 of the outer housing is positioned adjacent to the bottom surface 132 of the chest band segment 102.

FIG. 7 provides an enlarged, cross-section view of the vibrating element 108 of FIG. 6. This view more clearly illustrates an exemplary coupling between the housing for the vibrating element 108 and the chest band segment 102. As shown, the inner housing 138 may fit through an opening in the chest band segment 102, such that a first portion of the inner housing 138 is above the top surface 130 of the chest band segment 102 and a second portion of the inner housing 138 is below the bottom surface 132 of the chest band segment 102. The upper portion 134 of the outer housing may be secured to the first portion of the inner housing 138 that is above the top surface 130 of the chest band segment 102. Similarly, the lower portion 136 of the outer housing may be secured to the second portion of the inner housing 138 that is below the bottom surface 132 of the chest band segment 102. The outer housing portions may be secured to the inner housing 138 in any number of ways, such as gluing, snapping, clamping, threading, or any other means of securing the outer housing portions to the inner housing portions. As shown in FIG. 7, the upper portion 134 and the lower portion 136 of the outer housing may be positioned directly adjacent to the top surface 130 and the bottom surface 132, respectively, of the chest band segment 102. For example, the outer housing portions may pinch the chest band segment 102 such that the vibrating element does not slide up and down with respect to the chest band segment 12 during use. In other words, the vibrating element 108 may remain coupled to the chest band segment 102 in a fixed position during operation. This configuration may advantageously maintain the vibrating element in a vertical position, even as the mass 148 rotates and causes the vibrating element to vibrate. For example, as the vibrating element vibrates, it does not tip over; instead, it may remain substantially upright, such that the bottom end 164 of the vibrating element may remain adjacent to the user's body and may continue to provide a vibrational force to the user's body.

According to this exemplary configuration, if the position of the motor body 144 corresponds to the upper portion 134 of the outer housing, as maintained by the positioning rings 140 and 142 within the inner housing 138, the motor body 144 is positioned above the top surface 130 of the chest band segment 102. This is illustrated in FIG. 7. Additionally, if the motor body 144 is positioned in this way, the position of the mass 148 corresponds to the lower portion 136 of the outer housing. Thus, the mass 148 is positioned below the bottom surface 132 of the chest band segment. This is also illustrated in FIG. 7. In this example, when the vibrating element is secured to the chest band segment 102 at a point that falls between the motor body 144 and the mass 148, a pivot point may be created, where the vibrating element may rock and/or shake based on that pivot point. The exact positioning of the vibrating element may be adjusted to optimize this pivot point location, thereby optimizing the vibrational force that may be provided to the user's body, as well.

It will be understood that while an exemplary embodiment of a vibrating element coupled to a chest band segment is described with respect to various separate components, in other embodiments, certain parts may be machined particularly for use with the apparatus described herein. For example, a vibrating element may be machined such that it comprises components different in number and/or nature from those described above, but nonetheless provides the desired vibrating effect. All such variations are included within the scope hereof.

As mentioned, the chest band segment 102 may be comprised of any number of materials. A material selection may take into account a preference to maintain the vibrating elements in a vertical position.

Figure 11:
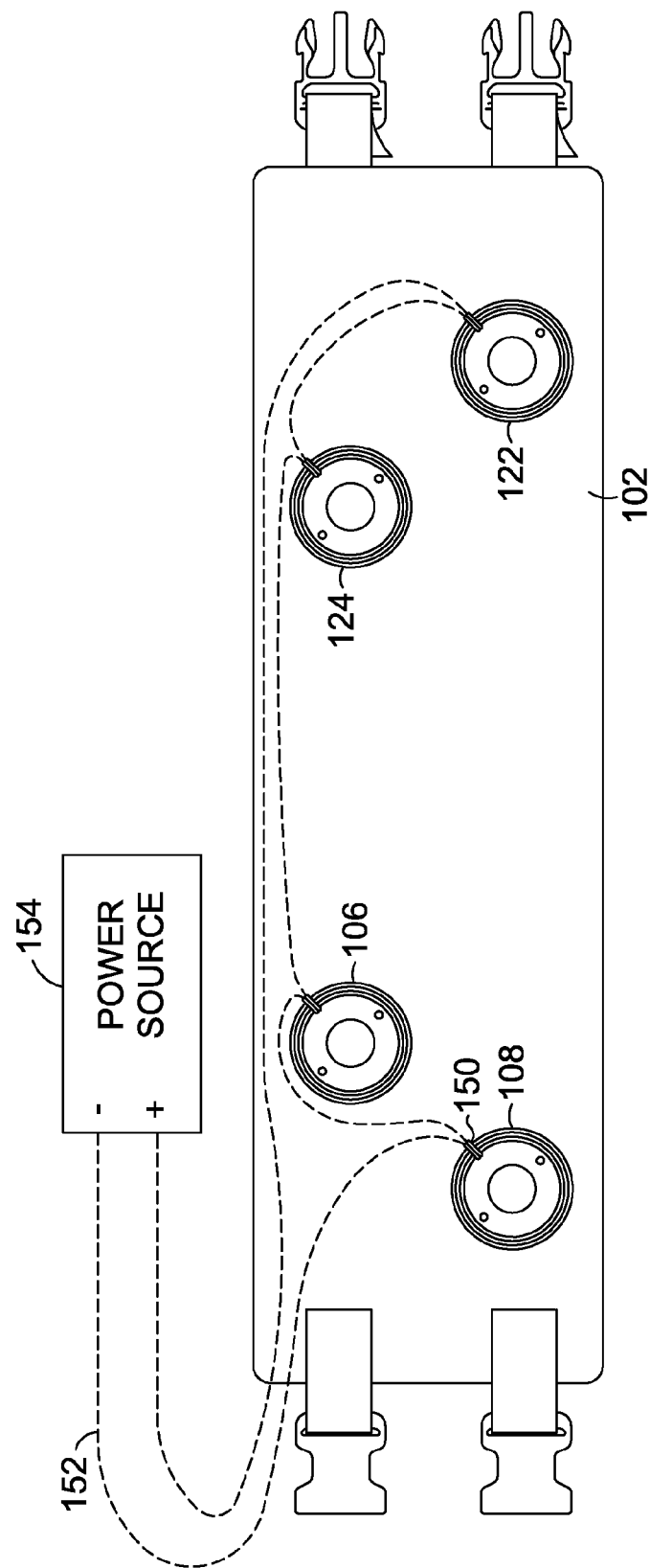
FIG. 11 is a plan view of a top surface of an exemplary chest band segment including vibrating elements, where each of the vibrating elements is electrically coupled to a power source, in accordance with an exemplary embodiment hereof.
Figure 12:
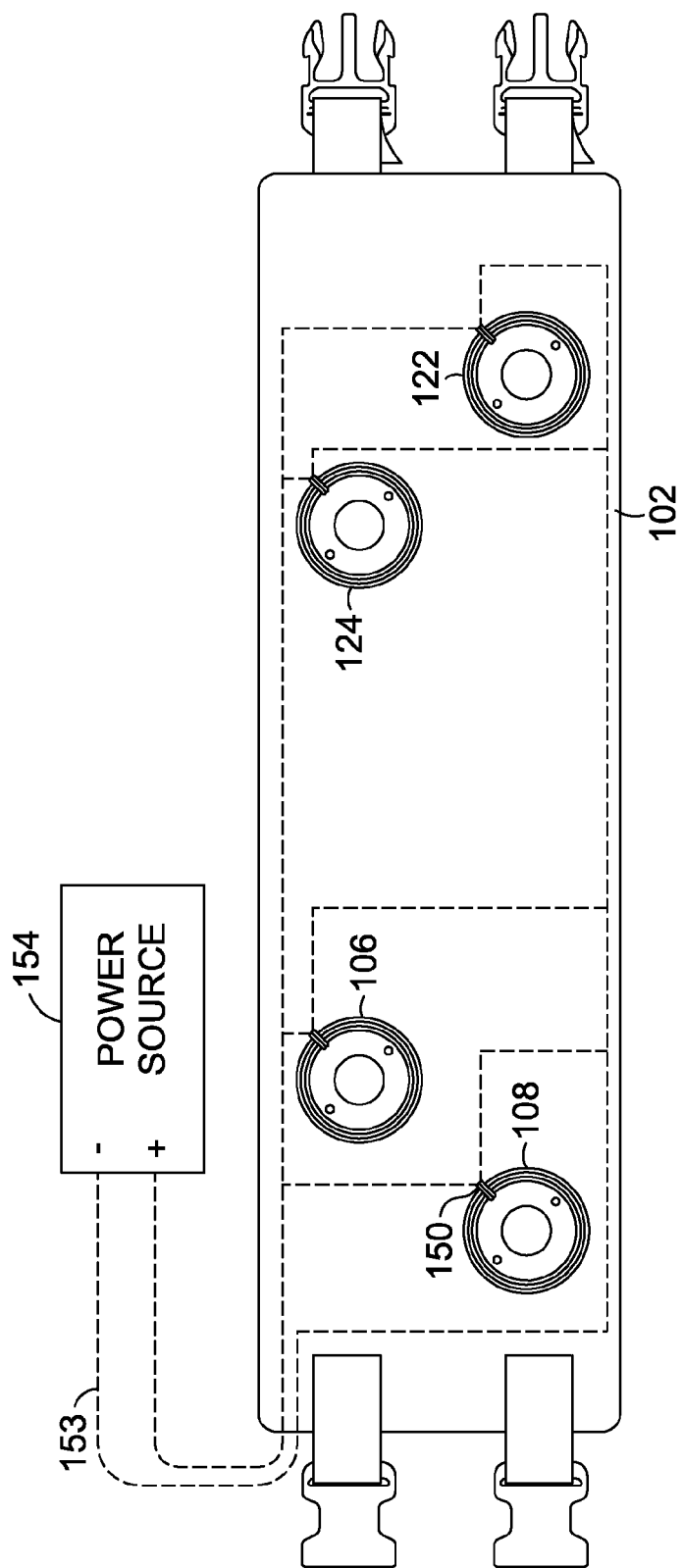
FIG. 12 is a plan view of a top surface of an exemplary chest band segment including vibrating elements, where each of the vibrating elements is electrically coupled to a power source, in accordance with an exemplary embodiment hereof.

Turning now to FIG. 11, a top-down plan view of the exemplary chest band segment 102 is provided. In particular, FIG. 11 illustrates the way in which multiple different vibrating elements may be electrically coupled to a single power source 154 by way of a series circuit 152. FIG. 12 illustrates the way in which multiple different vibrating elements may be electrically coupled to a single power source 154 by way of a parallel circuit 153. In either scenario, one or more wires may connect a power connection, such as the power connection 150 discussed with respect to FIGS. 6-10, to the power source 154. A selection of a series circuit 152 or a parallel circuit 153 may be based on considerations of battery life and motor effectiveness, among other things. A series circuit 152, for example, may provide for increased battery life (such as increased life of the power source 154) but decreased effectiveness of the vibrating element (such as a decreased effectiveness of a motor component included in a vibrating element). By contrast, a parallel circuit 153 may utilize the full potential of a vibrating element (such as the full potential of a motor component included in a vibrating element), but may cause the power source 154 to be drained more quickly. Additionally, in a parallel circuit 153, if one vibrating element fails, the remaining vibrating elements may continue to function properly. In a series circuit 152, if one vibrating element fails, then the remaining vibrating elements included in the circuit will not function properly, either. Accordingly, each circuit configuration is associated with various advantages and disadvantages.

The power source 154 of FIGS. 11-12 may include a rechargeable battery, such as a lithium-ion battery. As shown, the power source 154 may be external to the chest band segment 102. In some instances, the power source 154 may be integrated into the chest band segment 102. In additional instances, the vibrating elements may be coupled to multiple power sources. Any combination of the above is included within the scope hereof.

Figure 13:
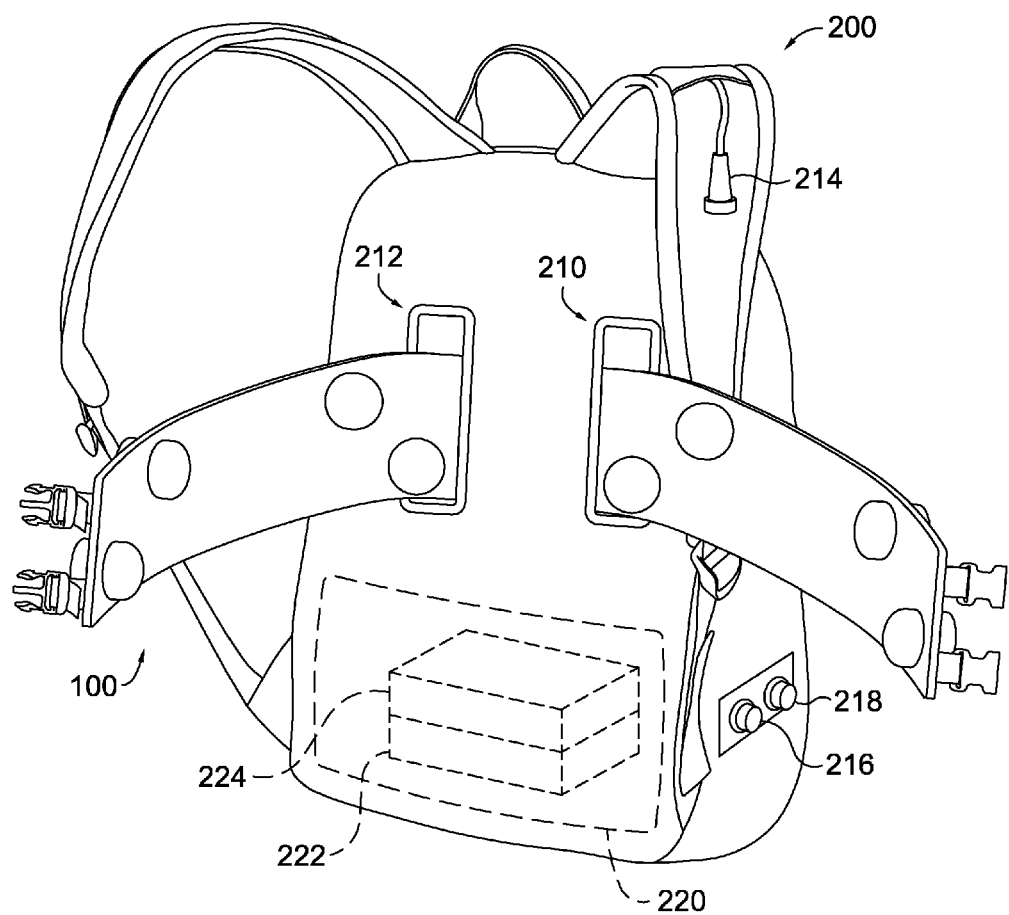
FIG. 13 is a rear, perspective view of an exemplary chest band coupled to an exemplary wearable pack, in accordance with an exemplary embodiment hereof.
Figure 14:
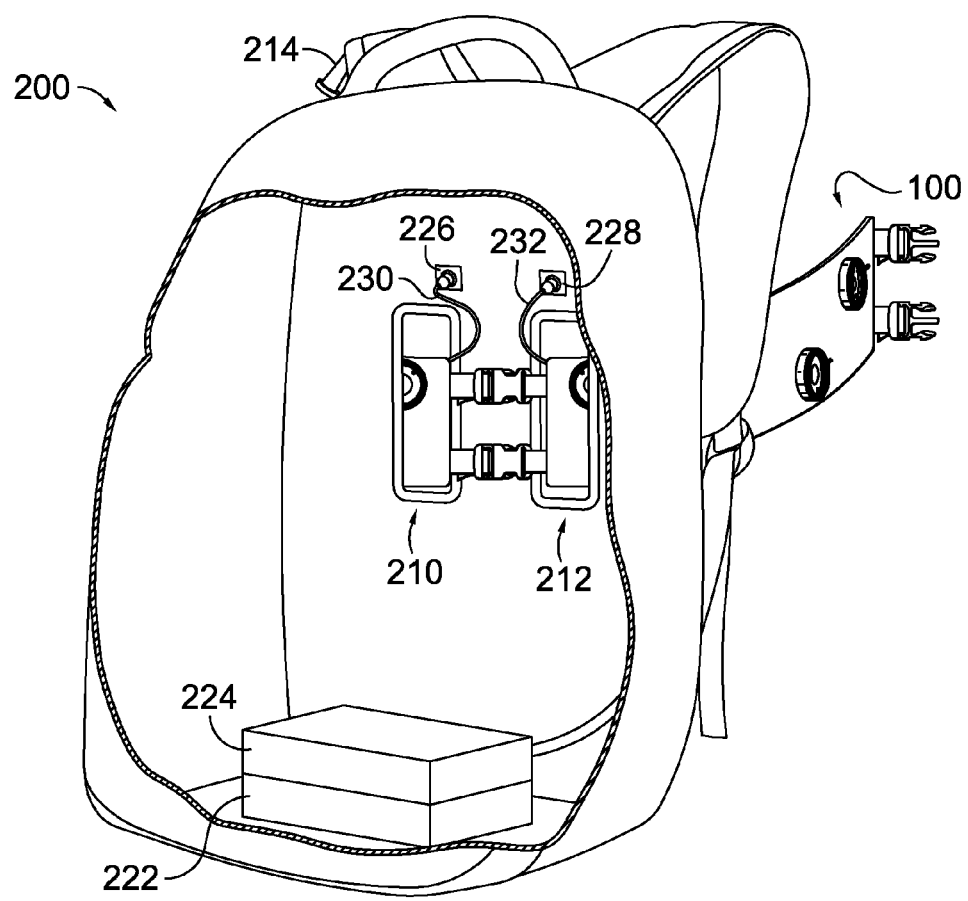
FIG. 14 is a cutaway view of an exemplary wearable pack coupled to an exemplary chest band, in accordance with an exemplary embodiment hereof.

As previously mentioned, a significant advantage of the apparatus described herein is that it is portable. In one example, this portability is enhanced by providing the components of the apparatus in conjunction with a wearable pack. A rear, perspective view of an exemplary wearable pack 200 is illustrated in FIG. 13 and a cutaway view showing an exemplary interior of the wearable pack 200 is illustrated in FIG. 14. The wearable pack 200 may be, for example, a backpack. Numerous other wearable packs are included within the scope hereof, including fanny packs, sling bags, shoulder bags, purses, and any other pack that may be worn and/or carried by a user. Additionally or alternatively, the apparatus may be integrated into a garment, such as a jacket, sweatshirt, vest, or other garment.

Figure 15:
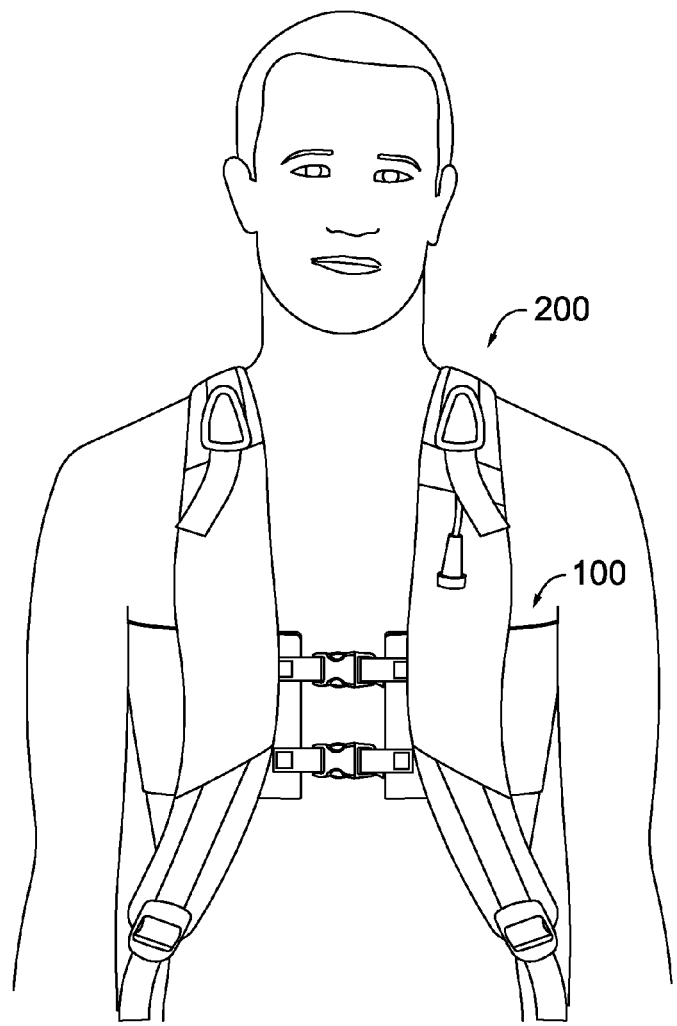
FIG. 15 is a front, perspective view of an exemplary chest band coupled to an exemplary wearable pack, where the combination of the chest band and the wearable pack is being worn by a user, in accordance with an exemplary embodiment hereof.

FIGS. 13-14 illustrate one exemplary way in which the chest band 100 may be coupled to the wearable pack 200. In this example, the chest band 100 slides through two chest band slots 210 and 212. The user may then fasten the chest band 100 around his chest and wear the wearable pack 200 on his back, as illustrated in FIG. 15.

As shown in FIG. 14, the chest band 100 may be electrically coupled to a power source 222. This exemplary electrical coupling may be achieved by plugging the power components 230 and 232 into the power ports 226 and 228, respectively. The power ports 226 and 228 may be electrically coupled to the power source 222. For example, one or more wires may run from the power ports 226 and 228 to the power source 222. These wires may be sewn into an interior wall of the wearable pack 200.

The chest band 100 and the power source 222 may further be electrically coupled to user input components 216 and 218. Thus, the operation of the vibrating elements included on the chest band 100 may be initiated and/or adjusted based on a user input received at user input component 216, for example. In one basic embodiment, the chest band 100, the user input component 216, and the power source 222 may operate to provide the chest therapy described herein. The user input component 216 may include a resistor, such as an analog resistor, a variable resistor, or a combination thereof, in order to provide a variety of operational settings (e.g., high, medium, or low vibrational intensity, as well as any number of intermediate settings). These components may be electrically coupled via a printed circuit board, for example. Because all of these components are relatively small and lightweight, they may be easily stored and/or transported, thereby providing enhanced mobility for the user.

In one example, the user input component 216 may enable a user to turn on the vibrating elements included in the chest band 100 and select a desired level of vibrational force. As mentioned, the user input component 216 may provide for any number of power settings. For example, six different settings associated with varying levels of vibrational intensity may be provided. As mentioned, the frequency of vibration provided by the vibrating elements may range from 5 hertz to 65 hertz, in some embodiments. In one example, a "low" setting may correspond to a frequency of 20 hertz and a "high" setting may correspond to a frequency of 50 hertz, where intermediate settings may correspond to frequencies between 20 hertz and 50 hertz. Thus, the same apparatus may provide a desired intensity of chest therapy to users of any number of ages and/or sizes. A small child, for example, might choose a low power setting, while a large adult might choose a high power setting. A user can thus choose a setting that is both effective and comfortable, according to his individual needs.

In addition to the chest band 100, the wearable pack 200 may include other therapy and/or treatment components. For example, a nebulizer treatment component 224 may be provided. The nebulizer treatment component 224 may include an air compressor connected to tubing that runs to a desired location on the wearable pack 200. An auxiliary attachment 214 may be connected to the end of the tubing. The auxiliary attachment 214 may be configured to attach to a nebulizer mouth piece. The wearable pack 200 may include an opening that allows the auxiliary attachment 214 to be accessed from the exterior of the wearable pack 200. For example, as shown in FIGS. 13-14, the auxiliary attachment 214 may be located at an exterior portion of a shoulder strap of the wearable pack 200, such that a user may easily attach a nebulizer mouth piece and conveniently engage in a nebulizer treatment. The nebulizer treatment component 224 may be electrically coupled to the power source 222, as well as the user input components 216 and 218. For example, the user input component 218 may allow a user to turn the nebulizer treatment component on and off.

Accordingly, the user input components 216 and 218 may allow a user to engage a desired operational setting of the chest band 100 and/or the nebulizer treatment component 224. Advantageously, the user may simultaneously engage in chest therapy using the chest band 100 and a nebulizer treatment using the nebulizer treatment component 224. And because the apparatus is designed to be portable, the user may engage in such therapy and treatment while performing any number of activities. For example, the apparatus may enable the user to engage in a chest therapy session and/or a nebulizer treatment while walking, running, biking, playing, or any other desired activity.

In additional embodiments, a programmable controller might also be electrically coupled to some or all of the components mentioned above. The controller may control the operation of the chest band 100, including the multiple vibrating elements, based on user input received at the user input component 216. The controller may be programmable to provide an expanded selection of operating settings. For example, the controller may provide any number of customized programs. One program might simultaneously engage all vibrating elements at the same power setting, thereby providing a similar vibrational force to the user's body from each vibrating element. Another program might selectively engage particular vibrating elements at customized power settings. For example, all vibrating elements might be simultaneously engaged, but the vibrational force provided by each vibrating element might vary. Additionally or alternatively, only a portion of the vibrating elements might be engaged at a particular point in time. The controller may further provide for timed programming, such that a particular program runs for a predetermined period of time. Any and all such combinations of the above are included within the scope hereof. The controller might also be electrically coupled to the nebulizer treatment component 224 and may provide customized operational settings for nebulizer treatments.

As shown in FIG. 13, the wearable pack 200 may include a compartment 220 for housing certain components, such as the power source 222 and the nebulizer treatment component 224. This compartment 220 may be a separate pocket included in the wearable pack 200, such that the components included therein are separated from other articles that may be stored in the wearable pack.

It will be understood that additional components might be included in an apparatus for providing chest therapy. For example, an alert component might remind a user that it is time to engage in a chest therapy and/or nebulizer treatment session. An alert provided by the alert component might include any combination of visual, audio, and/or tactile alerts. For example, a flashing light, a sounding alarm, and/or a vibration may remind a user that a predetermined period of time has elapsed since the last therapy and/or treatment session.

It should be noted that in the exemplary embodiment of FIGS. 13-14, the chest band 100 is both physically coupled and electrically coupled to the wearable pack 200 during use. However, the chest band 100 need not necessarily be physically attached to the wearable pack 200 in order for the chest band 100 to provide physical chest therapy. For example, if the wearable pack is a fanny pack, then the fanny pack may be worn around the user's waist, while the chest band 100 is worn separately around the user's chest. In this example, the chest band 100 may be electrically coupled to the fanny pack during operation, but need not be physically touching the fanny pack.

Furthermore, while exemplary embodiments above are discussed with respect to a wearable pack, in a further embodiment, the components required for operating the chest band 100 might be fully integrated into the chest band 100, itself. For example, a power source, a controller, and user input components might all be included in the chest band, such that a user can store and transport the chest band 100 in any way desired. Additionally, as mentioned, the components required for operating the chest band 100 and/or nebulizer treatment component 224 might be integrated into a garment, such as a jacket, sweatshirt, vest, or other article of clothing.

Turning now to FIG. 15, a front, perspective view is provided of the exemplary chest band 100 coupled to the exemplary wearable pack 200, where the combination of the chest band 100 and the wearable pack 200 is being worn by a user. In this exemplary embodiment, the chest band segments of the chest band 100 include covers that conceal the vibrating elements from view. Thus, the vibrating elements and any associated wiring may be hidden from view. In this instance, the connection components described above with respect to FIGS. 1-2 may be coupled to the cover material of the chest band segments. In addition to aesthetic considerations, chest band segments might include covers in order to enhance the comfort of the user while the chest band 100 is in use. For example, a cover comprising a particular material might make chest therapy sessions more comfortable for the user. The covers may be removable in some embodiments, such that a user may access the vibrating elements, wiring, and/or other components. This may facilitate maintenance and/or repairs, for example.

Figure 16:
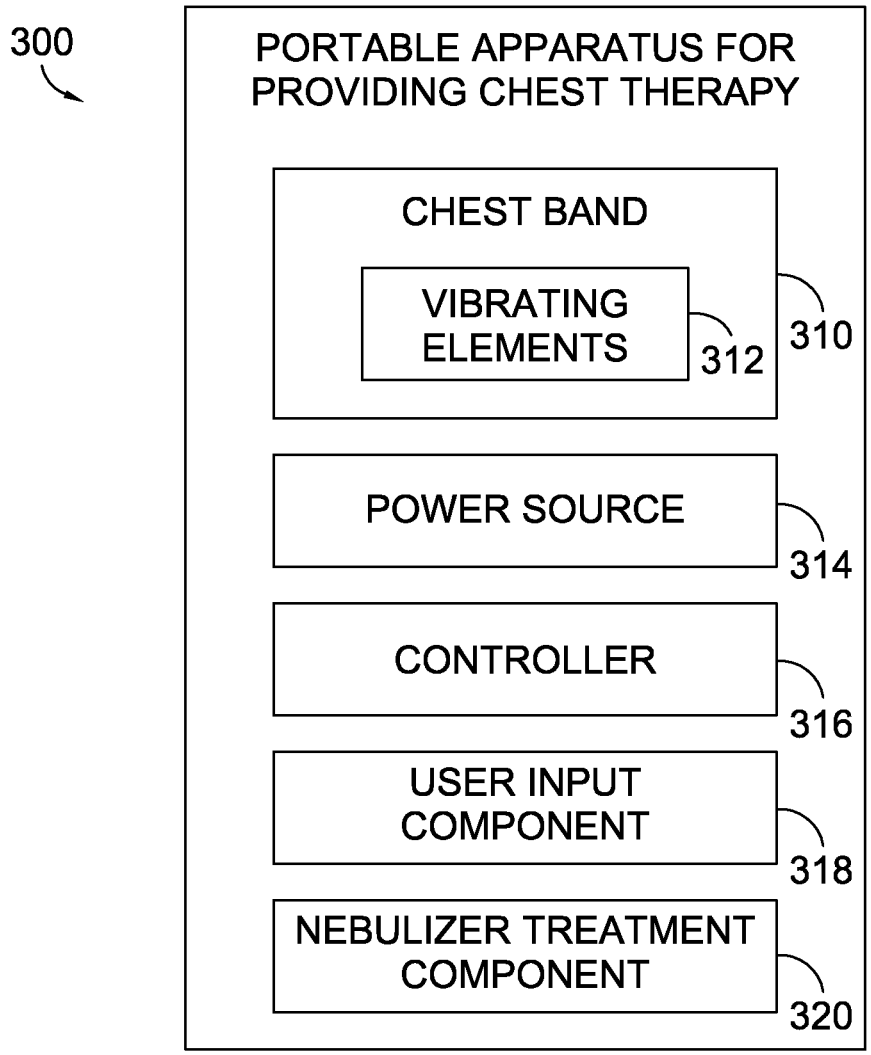
FIG. 16 is a block diagram showing exemplary components that may be included in an exemplary portable apparatus for providing chest physical therapy, in accordance with an exemplary embodiment hereof.

FIG. 16 provides a block diagram that shows exemplary components that may be included in an exemplary portable apparatus 300 for providing chest therapy. As previously discussed, the portable apparatus 300 may include a chest band 310 having one or more vibrating elements 312. The portable apparatus 300 may further include a power supply 314 and a controller 316. A user input component 318 and a nebulizer treatment component 320 may also be included. As described above, the controller 316 may control the operation of the chest band 310 and the nebulizer treatment component 320 based on a user input received at the user input component 318. It will be understood that the components illustrated in FIG. 16 are exemplary in nature and in number and should not be construed as limiting. Any number of components may be employed to achieve the functionality described herein. Components in addition to those illustrated in FIG. 16 may also be included within the apparatus 300 and are included within the scope hereof.

As described above, a portable apparatus for providing chest therapy to a user may include a controller that controls various operations of the apparatus. The controller may be, for example, a computing device, such as the exemplary computing device 400 of FIG. 17. Accordingly, embodiments of the invention may be described in the general context of computer code or machine useable instructions, including computer executable instructions, such as program modules, being executed by a computer or other machine. Generally, program modules including routines, programs, objects, components, data structures, etc., refer to code that performs particular tasks or implements particular abstract data types. Embodiments hereof may be practiced in a variety of system configurations, including hand held devices, consumer electronics, general purpose computers, more specialty computing devices, etc. Moreover, embodiments hereof may also be practiced in a distributed computing system where tasks are performed by separate or remote-processing devices that are linked through a communications network. Computing device 400 is but one example of a suitable operating environment and is not intended to suggest any limitation as to the scope of use or functionality of embodiments hereof. The computing device 400 should not be interpreted as having any dependency or requirement relating to any one component nor any combination of components illustrated.

Figure 17:
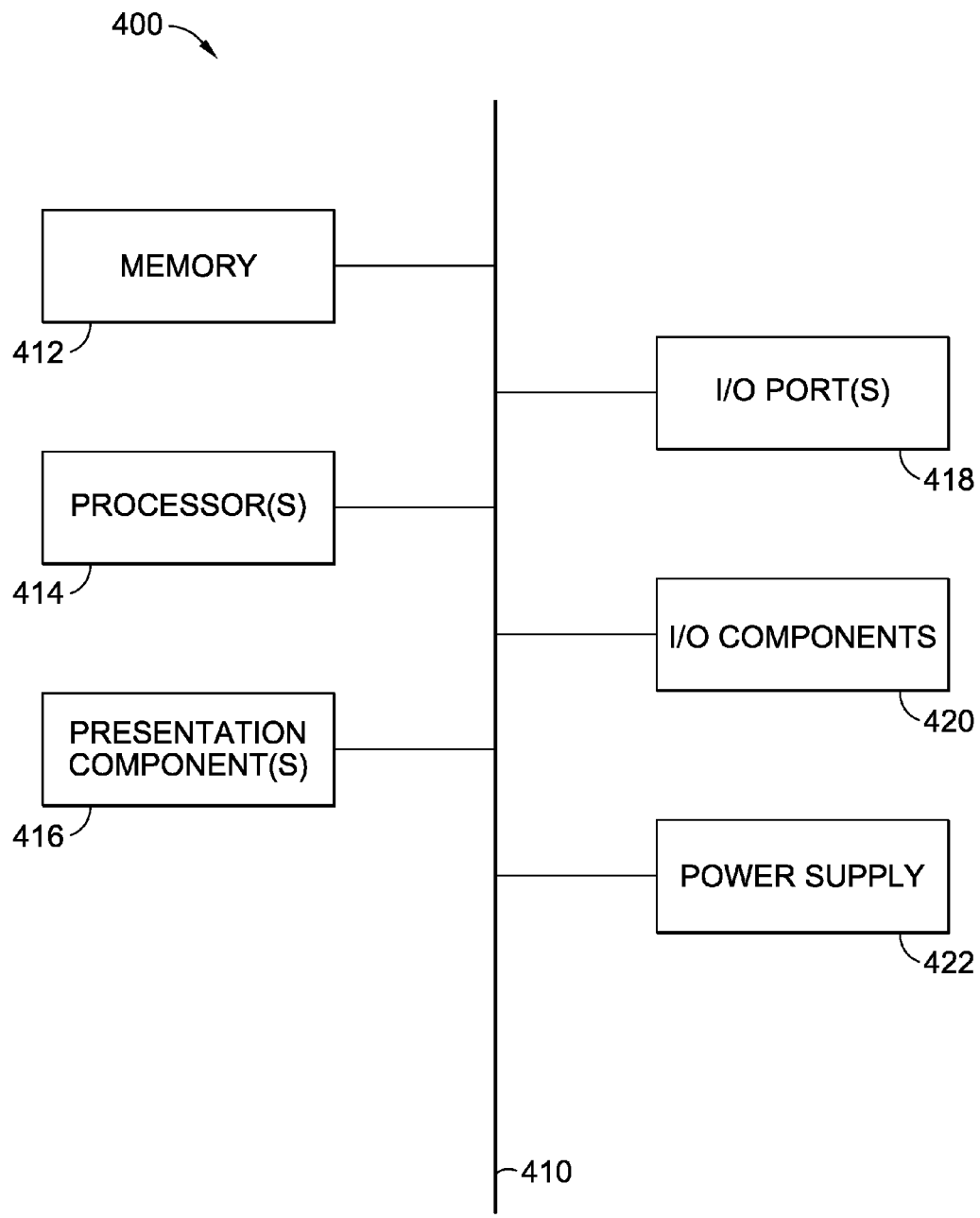
FIG. 17 is a block diagram of an exemplary computing device that may be used in conjunction with a portable apparatus for providing chest physical therapy, in accordance with an exemplary embodiment hereof.

As shown in the example of FIG. 17, the computing device 400 may have a bus 410 that directly or indirectly couples the following components: a memory 412, one or more processors 414, one or more presentation components 416, one or more input/output (I/O) ports 418, one or more I/O components 420, and an illustrative power supply 422. Bus 410 represents what may be one or more buses (such as an address bus, data bus, or combination thereof). Although the various components of FIG. 17 are shown with lines for the sake of clarity, in reality, delineating various components may not be so clear. For example, a presentation component, such as a display device, may be considered to be an I/O component. Additionally, processors may have memory.

The power supply 422 might include a rechargeable battery. For example, the power supply 422 may be a rechargeable battery that provides power to various components of a portable apparatus, including the vibrating elements, the nebulizer treatment component, and the controller, among others. As mentioned above, the rechargeable battery may be a lithium-ion battery of a desired voltage. As will be understood, the components of exemplary computing device 400 may be used in connection with one or more embodiments of the invention. In embodiments, computing device 400 may include fewer components than those depicted in FIG. 17, or other components in addition to those depicted in FIG. 17.

Computing device 400 typically may have a variety of non-transitory computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices, carrier wave or any other medium that can be used to encode desired information and be accessed by computing device 400.

Memory 412 may be comprised of tangible computer-storage media in the form of volatile and/or nonvolatile memory. Memory 412 may be removable, nonremovable, or a combination thereof. Exemplary hardware devices include solid-state memory, hard drives, optical-disc drives, etc.

Computing device 400 is depicted to have one or more processors 414 that read data from various entities such as memory 412 or I/O components 420. Exemplary data that is read by a processor may be comprised of computer code or machine-useable instructions, which may be computer-executable instructions such as program modules, being executed by a computer or other machine.

Presentation component(s) 416 may present data indications to a user or other device. Exemplary presentation components include a display device, speaker, printing component, vibrating component, light-emitting component, etc. I/O ports 418 allow computing device 400 to be logically coupled to other devices including I/O components 420, some of which may be built in.

In the context of embodiments hereof, the computing device 400 may be used to control various components included in a portable apparatus for providing chest therapy to a user. For example, the controller discussed above may include at least some of the components of computing device 400.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. A portable apparatus for providing chest therapy to a user, the portable apparatus comprising:
    a chest band comprising one or more chest band segments, wherein the chest band is configured to be worn around a chest of the user;
    a plurality of vibrating elements coupled to the one or more chest band segments, each of the plurality of vibrating elements comprising a motor coupled to an asymmetric mass, wherein for each of the plurality of vibrating elements, the motor is disposed above a top surface of one of the one or more chest band segments and the asymmetric mass is disposed below a bottom surface of the one of the one or more chest band segments; and
    a user input component for receiving a user input regarding an operation of the plurality of vibrating elements, wherein the user input component is coupled to the plurality of vibrating elements.

2. The portable apparatus of claim 1 further comprising a controller that is programmable to control the plurality of vibrating elements based on the user input received at the user input component, wherein the controller is coupled to the user input component and the plurality of vibrating elements.

3. The portable apparatus of claim 1, further comprising a wearable pack and a nebulizer treatment component coupled to the wearable pack, wherein the portable apparatus enables operating the nebulizer treatment component concurrently with providing a vibrational force by the plurality of vibrating elements.

4. The portable apparatus of claim 1, wherein the plurality of vibrating elements is arranged such that when the chest band is worn around the chest of the user, a first vibrating element of the plurality of vibrating elements is disposed at an upper lateral area of the chest of the user and a second vibrating element of the plurality of vibrating elements is disposed lower than the first vibrating element at a medial area of the chest of the user.

5. The portable apparatus of claim 4, wherein the plurality of vibrating elements is arranged such that when the chest band is worn around the chest of the user, a third vibrating element of the plurality of vibrating elements is disposed at an upper lateral area of the back of the user and a fourth vibrating element of the plurality of vibrating elements is disposed lower than the third vibrating element at a medial area of the back of the user.

6. The portable apparatus of claim 1, wherein the one or more chest band segments include at least two chest band segments that are removably coupled to one another, the at least two chest band segments forming a continuous circumferential chest band.

7. The portable apparatus of claim 6, wherein the at least two chest band segments are removably coupled to one another by a connection component comprising a strap and a buckle, the strap comprising an elastic material.

8. A portable apparatus for providing chest therapy to a user, the portable apparatus comprising:
    an elastic belt configured to wrap around a chest of the user;
    a chest band segment that is mounted on the elastic belt, the chest band segment including a top surface parallel to an opposite bottom surface, the bottom surface configured to be positioned adjacent to a body of the user; and
    a plurality of vibrating elements coupled to the chest band segment, wherein each of the plurality of vibrating elements comprises a motor coupled to an asymmetric mass, and wherein the motor of each vibrating element is disposed above the top surface of the chest band segment and the asymmetric mass of each vibrating element is disposed below the bottom surface of the chest band segment.

9. The portable apparatus of claim 8, wherein the motor is coupled to the asymmetric mass via a shaft, wherein each of the plurality of vibrating elements is maintained in a vertical position with respect to the bottom surface of the chest band segment, and wherein the vertical position is characterized by the shaft of each of the plurality of vibrating elements being approximately perpendicular to the bottom surface of the chest band segment.

10. The portable apparatus of claim 9, wherein each of the plurality of vibrating elements extends through the top surface and the bottom surface of the chest band segment.

11. The portable apparatus of claim 10, wherein each of the plurality of vibrating elements includes a housing, wherein the chest band segment bisects the housing of each of the plurality of vibrating elements, a portion of the housing that is disposed above the chest band segment comprising an upper portion of the housing and a portion of the housing that is disposed below the chest band segment comprising a lower portion of the housing, and wherein an entirety of the motor is disposed in the upper portion of the housing and an entirety of the asymmetric mass is disposed in the lower portion of the housing.

12. The portable apparatus of claim 11, wherein the lower portion of the housing comprises a rounded cap.

13. The portable apparatus of claim 8, further comprising a backpack, wherein a rear surface of the backpack includes an opening that receives the chest band segment and maintains the chest band segment in a fixed vertical position with respect to the backpack.

14. The portable apparatus of claim 8, wherein the plurality of vibrating elements is arranged such that when the chest band segment is positioned adjacent to the body of the user, a first vibrating element of the plurality of vibrating elements is disposed at an upper lateral area of the chest of the user and a second vibrating element of the plurality of vibrating elements is disposed lower than the first vibrating element at a medial area of the chest of the user.

15. The portable apparatus of claim 14, wherein the plurality of vibrating elements is arranged such that when the chest band segment is positioned adjacent to the body of the user, a third vibrating element of the plurality of vibrating elements is disposed at an upper lateral area of the back of the user and a fourth vibrating element of the plurality of vibrating elements is disposed lower than the third vibrating element at a medial area of the back of the user.

16. An article of manufacture comprising:
   an elastic belt configured to wrap around a chest of a user;
   a panel that is mounted on the elastic belt, the panel having a top surface that is parallel to an opposite bottom surface; and
   a vibrating element coupled to the panel, the vibrating element comprising a motor, a shaft, and a mass, wherein the motor is disposed above the top surface of the panel and the mass is disposed below the bottom surface of the panel.

17. The article of manufacture of claim 16, wherein the vibrating element extends vertically through the top surface and the bottom surface of the panel.

18. The article of manufacture of claim 16, wherein the panel is rectangular in shape.

19. The article of manufacture of claim 16, wherein the motor, the shaft, and the mass are contained within a vibrating element housing, and wherein the article of manufacture further comprises a cover for the panel, the cover concealing both the panel and the vibrating element housing.

20. The article of manufacture of claim 16, further comprising a wearable pack that houses a power source, wherein the vibrating element is electrically coupled to the power source via a power port on the wearable pack.

* * * * *